United States Patent [19]
Espevik et al.

[11] Patent Number: 6,087,342
[45] Date of Patent: Jul. 11, 2000

[54] SUBSTRATES HAVING BOUND POLYSACCHARIDES AND BACTERIAL NUCLEIC ACIDS

[75] Inventors: Terje Espevik; Gudmund Skjåk-Bræk, both of Trondheim, Norway

[73] Assignee: FMC Biopolymer AS, Drammen, Norway

[21] Appl. No.: 09/079,859

[22] Filed: May 15, 1998

[51] Int. Cl.[7] .......................... A61K 31/70; C08B 11/00; C07H 21/02
[52] U.S. Cl. ................................. 514/44; 514/23; 514/42; 514/43; 514/53; 514/54; 536/1.11; 536/22.1; 536/23.1; 536/123.1
[58] Field of Search ................................. 514/34, 42, 23, 514/43, 44, 53, 54; 536/123.1, 22.1, 23.1, 1.11

[56] References Cited

U.S. PATENT DOCUMENTS 5,166,137  11/1992  Otterlei et al. ............................ 514/23

FOREIGN PATENT DOCUMENTS

| | | |
|---|---|---|
| 0212039 | 3/1987 | European Pat. Off. . |
| 0277697 | 8/1988 | European Pat. Off. . |
| 1544908 | 4/1979 | United Kingdom . |
| 1571992 | 7/1980 | United Kingdom . |

OTHER PUBLICATIONS

Espevik et al., "The involvement of CD14 in stimulation of cytokine production by uronic acid polymers", Eur. J. Immunol. 1993, 23:255–261.

Otterlei et al., "Similar Mechanisms of Action of Defined Polysaccharides and Lipopolysaccharides: Characterization of Binding and Tumor Necrosis Factor Alpha Induction", Infection And Immunity, May 1993, p. 1917–1925.

Ugelstad, et al., "Preparation And Application Of New Monosized Polymer Particles", Progress in Polymer Science, vol. 17, No. 1, pp. 87–161.

Rietschel et al., "Bacterial Endotoxin: Molecular Relationships Between Structure and Activity", Infectious Disease Clinics of North America, vol. 5, No. 4, Dec. 1991, pp. 753–779.

Hermanson et al. "Immobilized Affinity Ligand Techniques", Academic Press, Inc., 1992, pp. 80–85.

Seljelid et al., "The Protective Effect of β1–3D–Glucan–Derivatized Plastic Beads against *Escherichia coli* Infection in Mice", Scand. J. Immunol. 25, 55–60, 1987.

Rasmussen et al., "Novel Immunomodulators With Pronounced In Vivo Effects Caused by Stimulation of Cytokine Release", Journal of Cellular Biochemistry 46:60–68 (1991).

*Primary Examiner*—Elli Peselev
*Attorney, Agent, or Firm*—Wenderoth, Lind & Ponack, L.L.P.

[57] ABSTRACT

The cytokine stimulating effects of immune- stimulating polysaccharides and bacterial nucleic acids, and of lower molecular weight fragments thereof, is potentiated by coupling the immune-stimulating bioactive substance to the surface of a substrate, which is preferably in particulate form.

39 Claims, 5 Drawing Sheets

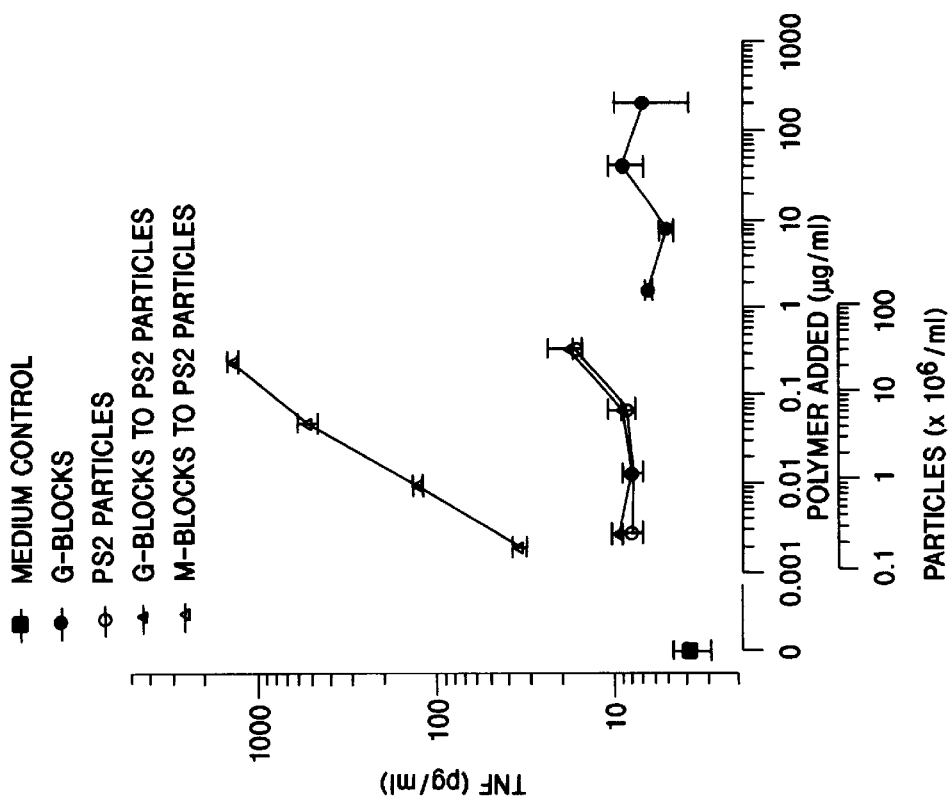
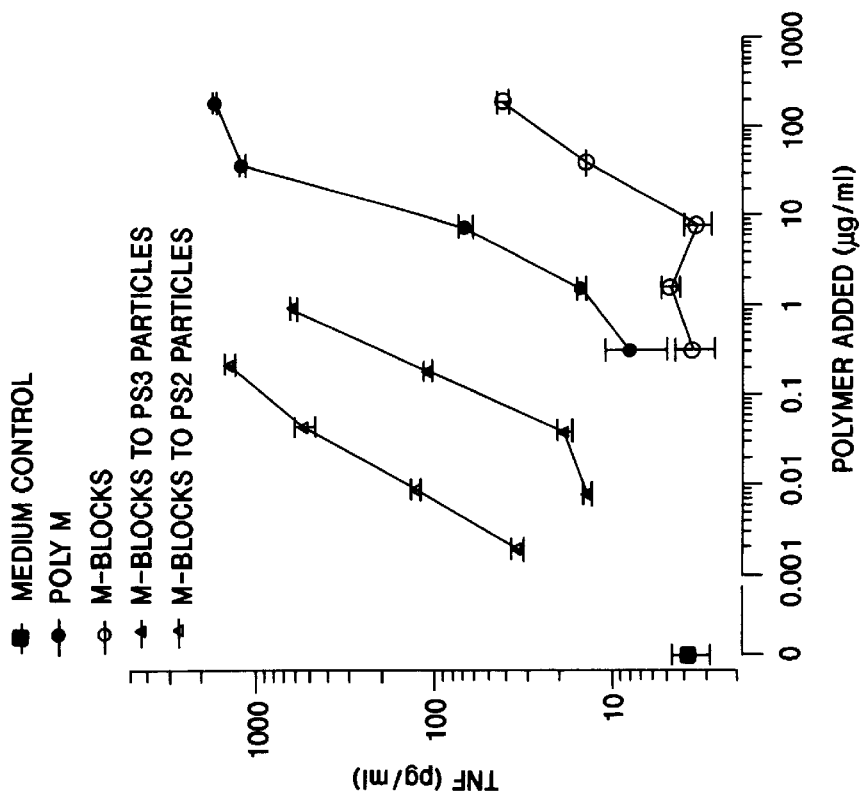
FIG. 1B
FIG. 1A

SUBSTRATES HAVING BOUND POLYSACCHARIDES AND BACTERIAL NUCLEIC ACIDS

BACKGROUND OF THE INVENTION

This invention relates to polysaccharides and bacterial nucleic acids which are capable of stimulating an immune response, and more particularly to substrate materials which potentiate that immune response. In specific and preferred embodiments of the invention, low molecular weight fragments of longer chain immune- stimulating polysaccharides and bacterial nucleic acids which have only a low bioactivity, as compared to the parent substance from which they are derived, are potentiated sufficiently so as to permit their use in substitution for the parent compound.

It is known that different uronic acid polymers with a β1–4 glycosidic linkage are able to stimulate monocytes to produce tumour necrosis factor (TNF) through a membrane CD14 dependent manner (Espevik et al, *Eur. J. Immunol.* 23:255). Mannuronan (poly M) is the most potent of the β1–4 linked uronic acid polymers in inducing cytokine production. However, the cytokine stimulatory activity of mannuronan is dependent of the molecular weight of the polymer, and optimal cytokine induction is obtained when the MW is 50,000 or higher (Otterlie et al, *Infect. Immun.* 61: 1993 pages 1917–1925. However, there is a sharp decline in activity at lower molecular weights and all useful activity is lost at a molecular weight below 10,000 g/mol. Although there are no apparent toxic effects when high molecular weight mannuronan is injected into mice, nonetheless it is important to use a polymer size as small as possible for therapeutic purposes in order to promote more complete and rapid excretion of the injected material from the body. This requirement therefore conflicts with the desire to optimise the TNF stimulating activity.

It is also known that lipopolysaccharide (LPS) has a TNF-inducing ability which depends on the three- dimensional supramolecular structure (Rietschel et al, "Bacterial endotoxins: properties and structure of biologically active domains", Werlag Chemie, 1988, p1). These supramolecular structures depend on the amount and distribution of the acyl chains in the lipid A region of LPS, and when lipid A occurs in a cubic or inverted hexagonal structure an increased cytokine induction is observed, whereas a lamella structure gives no cytokine induction. LPS as such is highly toxic but it can be delipidized by alkaline hydrolysis to form a detoxified LPS (D-LPS) from which the lipid A region, which is the main cause of the toxicity, has been removed. However, D-LPS has only a low ability to stimulate monocytes to produce TNF, despite retaining an intact polysaccharide portion.

It is disclosed by Seljelid et al of the Institute of Medical Biology, University of Tromsø, Norway in Scand. *J. Immunol.* 25, 55–60, (1987) that plastic microbeads derivatized with β-1,3-D glucan protect mice against pneumococcal and *E. coli* infections. These and other workers at the Institute of Medical Biology have subsequently shown that this protective effect is caused at least in part by stimulation of cytokine release (see, for example, Rasmussen et al, *Journal of Cellular Biochemistry* (1991) 46:60–68).

Other members of the family of polymers of uronic acid are also known to stimulate monocytes to produce TNF or other cytokines. For instance, D-glucuronic acid (D-GlcA) has this property, although with less potency compared with mannuronan.

Polysaccharides from gram-negative and gram- positive bacteria such as lipoarabinomannan, lipoteichoic acid and peptidoglycans are also known to induce cytokines.

Another well known immune-stimulating polysaccharide is chitosan.

It is, however, to be understood that not all polysaccharides have the ability to stimulate monocytes.

Certain bacterial nucleic acids form another category of substances with the capability of stimulating an immune response.

SUMMARY OF THE INVENTION

We have now found, in accordance with the present invention, that the cytokine-inducing activity of many immune-stimulating polysaccharides and bacterial nucleic acids, as well as of lower molecular weight fragments thereof, can be improved by binding the polysaccharides to the surfaces of a substrate. This surprising discovery not only helps to overcome the problems discussed above with using mannuronan and D-LPS, for example, in therapy, but more generally opens up new therapeutic possibilities not hitherto available.

In accordance with the present invention there is provided a substrate material to a surface of which is bound an immune-stimulating polysaccharide, other than β-1,3-D glucan, or a bacterial nucleic acid.

The present invention also provides a method for potentiating the cytokine-stimulating effect of an immune-stimulating polysaccharide, other than β-1,3-D glucan, or of an immune-stimulating bacterial nucleic acid, wherein said polysaccharide or nucleic acid is contacted with a substrate so as to become bound to a surface thereof.

BRIEF DESCRIPTION OF THE DRAWINGS

FIGS. 1A, 1B, 2A and 2B show results for TNS assays on products in Example 1, Comparative Example 1 and Example 2 below.

DETAILED DESCRIPTION OF THE INVENTION

Figure 2B:
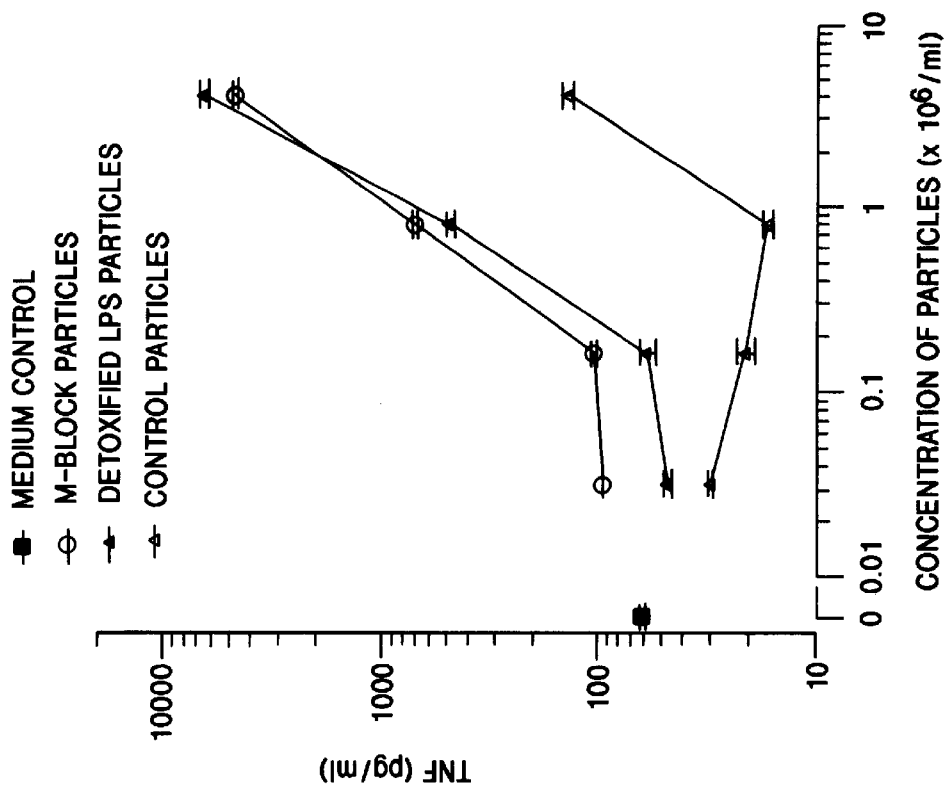

The present invention provides a new approach to potentiating the cytokine stimulating activity of polysaccharides and bacterial nucleic acids. In particular, to the best of our knowledge it has not hitherto been disclosed that lower molecular weight fragments of immune-stimulating polysaccharides and bacterial nucleic acids which have only relatively poor cytokine stimulating properties, as compared to their parent compound, may, by means of being bound to the surface of a substrate as disclosed herein, have their activity increased to a level which permits the use of the fragments in place of the parent compounds. The magnitude of the potentiation of the cytokine- stimulating activity which is achievable in accordance with this invention is illustrated in the Examples below.

It is therefore to be understood that the term "immune-stimulating polysaccharides and bacterial nucleic acids", and similar terms, includes within its scope lower molecular weight fragments of such polysaccharides and nucleic acids which retain at least some residual cytokine-stimulating activity. Preferably these polysaccharide and nucleic acid fragments contain from 2 to 100, more preferably from 10–30, sugar units. Polysaccharides fragments which contain from 2 up to about 7 sugar units are often considered to be, and are termed, oligomers (oligo-saccharides).

The bioactive substance may be, for example, a 1–4 linked uronic acid polymer, and may contain, for example, more than 80% mannuronic acid residues.

Although, as already stated, the invention has particular applicability to the potentiation of polysaccharide and nucleic acid fragments, it may also be used to potentiate the cytokine-stimulating activity of the immune-stimulating polysaccharides and bacterial nucleic acids themselves.

It appears from our studies that the form and nature of the substrate which is used as carrier for the active polysaccharide or nucleic acid material is not especially critical. For some purposes, it is desirable that the substrate should be in particulate form, for example for intravenous or subcutaneous injection, but in other cases the substrate could take the form of a body for implantation in vivo. In yet other cases, the substrate could be a material over which, for instance, a fluid could be brought into contact to achieve a reaction with the bound bioactive material.

Similarly, a wide range of different natural or synthetic materials may be used as the substrate. It will, of course, be understood that the substrate material must not cause unwanted reactions in the environment in which it is to be used.

In the experiments which are described in the Examples below we used magnetic monodisperse polystyrene particles made by the active swelling technique described by Ugelstad et al in *Progress in Polymer Science,* 17, No. 1, 87–161 (1992). Epoxy groups were introduced on the surface of the particles, and different amounts of amino linkers were then coupled to the epoxy surface by the method of Hermanson et al in Immobilized Affinity Ligand Techniques, Academic Press, New York 1992.

For some purposes, it is preferred that the substrate should be constituted by materials capable of being absorbed in vivo. A wide range of bioerodible and resorbable polymeric and other solid materials are known to the art.

Other natural or synthetic materials which could be used as the substrate in this invention will readily suggest themselves to those skilled in the art.

The size of substrate particles can vary widely, depending on the intended end use. For example, particles for subcutaneous injection can have a size up to 50 $\mu$m but preferably less than 20 $\mu$m, although for intravenous injection the particle size should be less than 5 $\mu$m. The shape of the particles used as substrate material is not critical.

The bioactive polysaccharide or nucleic acid component may be linked to the substrate in many different ways. For instance, a polysaccharide may be linked covalently by coupling through hydroxyl groups (always present in carbohydrates), carbonyl groups, amine groups (amino sugars) and carboxyl groups (uronic acids), or through substituents such as sulphate or phosphate groups, as appropriate. If required, linkers for covalent coupling can be applied to a substrate surface lacking groups capable of entering into covalent bonding with the bioactive component.

Some examples of covalent coupling chemistry useful herein are:

Carbonyl reactive chemistry
Carbonyl groups, either aldehydes or ketone on reducing sugars.
Aldehydes groups can also be introduced easily by periodate oxidation.

Example: Hydrazide activation

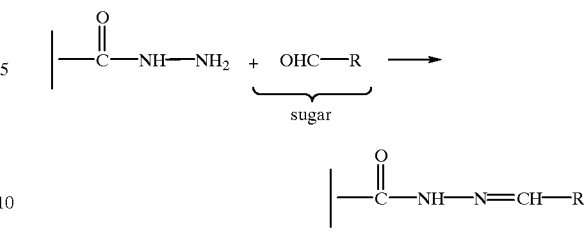

Example: Reductive amination using cyanoborohydride

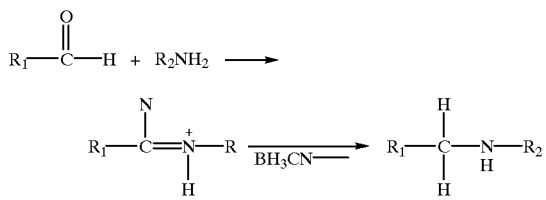

Hydroxyl reactive chemistry
Example: Polysaccharides can be activated with CNBr which then easily can be coupled to any ligand containing primary amines.

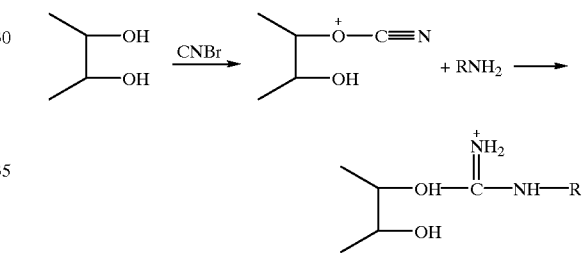

Example: Epoxy activated surfaces react with hydroxyl or amine groups at high pH and are well suited for carbohydrate coupling.

Carboxyl reactive chemistry
An example based on carbodiimide is described in the Examples below.

Although covalent coupling of the polysaccharide or nucleic acid is often preferred, it is also possible to bind the bioactive component to the substrate non-covalently. For example, coupling can be achieved by ionic or hydrophobic interactions, or by means of biospecificity (e.g. enzyme substrate antigen antibody).

The density of the bioactive polysaccharide or nucleic acid material bound on the surface of the particles or other substrate material is selected having regard to the intended use of the resulting composition. Generally, the density will lie in the range of 0.1 to 100 ng/$\mu$m$^2$, preferably in the range 0.1 to 50 ng/$\mu$m$^2$.

There is some evidence that there may, for any given polysaccharide or nucleic acid, be an optimum density to achieve maximum cytokine production, but further work is needed to confirm whether or not this is the case.

Although we do not wish to be bound by theory, our work indicates that when M-blocks or detoxified LPS, for example, are bound to a substrate surface, multiple membrane receptors may be aggregated which can synergize the induction of TNF.

The substrate materials of this invention are expected to find many uses in medicine. For example short blocks of mannuronan covalently linked to biodegradable particles can be used as an immunostimulator for the treatment of various types of diseases, for instance those in which patients will benefit from an enhanced cellular immunity, achieved through increased cytokine production.

Further, substrate materials of this invention can be used as an immunostimulator for protecting a patient who is about to undergo major surgery from infection from gram-positive or gram-negative bacteria. Another potential use of the present materials is as an immunostimulator to protect a patient who is about to undergo radiation therapy which damages bone marrow cells. The administration of, for instance, poly M-bound particles in accordance with this invention will lead to enhanced hematopoiesis.

The substrate materials of this invention may also be used as targeting anti-cancer drugs. Tumour cells are known to produce inhibiting factors for macrophages, but this may be reversed or depressed through the administration of, for instance, poly M-bound particles which have a stimulating effect on macrophages.

Particles to which are bound polysaccharides and bacterial nucleic acids in accordance with this invention may be administered, for example, by intravenous or subcutaneous injection. For this purpose the particles can be formulated with a pharmaceutically acceptable injectable carrier, for example a physiological buffer.

The invention is illustrated by the Examples which follow.
Materials and Methods Poly M was isolated from agar colonies of *Pseudomonas aeruginosa* 8830, which was grown at 18° C. as described by Gross et al, *J. Phytophatol,* 1983, 118:276: $^{14}$C-labelled fructose (Amersham, Buckinghamshire, England) was supplemented to the medium to make the alginate radioactive. The material was purified by a repeated combination of alkali treatment with 0.2M NaOH at 45° C., precipitation with ethanol, and extraction of the precipitate by ethanol and chloroform. The polymer was dissolved in pyrogen-free water, filtered through 0.22 μm membrane filter (Millipore) and lyophilized. LPS contamination in poly M was measured by LAL assay (Chromogenix AB, Mölndal, Sweden). The level of endotoxin in the polymer was <0.25 ng/mg. The content of mannuronic acid was estimated to be 92% by $^1$H-NMR spectroscopy Grasdalen et al, *Carbohydr. Res.* 1979, 68:23 and Grasdalen, *Carbohydr. Res.* 1979, 68:23), and the average molecular weight was estimated to be 350,000 g/mol by viscometry (Scott-Geräite). M-blocks (94% D-ManA) were prepared by hydrolysis of poly M for 1 hr at 100° C. at pH 5.6 and 1 hour at 100° C. at pH 3.8. This procedure yielded M-blocks with an average MW 5500 and 94% D-ManA. For some experiments M-blocks with an average MW of 3000 were produced by additional hydrolysis.

G-blocks (94% L-GulA and degree of polymerisation, 27) were isolated from colonies of *Azotobacter vinelandii* grown at 37° C. with $^{14}$C-labelled fructose (Skjak-Bræk et al, *Carbohydr. Res.* 1982, 103:133). Such G-blocks do not have any immune- stimulating properties.

C60XY (β1–4 linked glucuronic acid [D-GlcA] was prepared by oxidation of cellulose at position C-6 (*Painter, Corb. Res.* 55, 95–103, 1977). The average MW was estimated from intrinsic viscosity measurement to be 30,000, and the degree of oxidation (88% D-GlcA and 12% D-Glc) was determined by titration (Nevell, *Methods Carbohydr. Chem.* 1963, 3:161 and Yackel et al, *JACS* 1942, 64:121).

Endotoxin contamination in the different polysaccharides was measured by the Limulus amebocyte lysate (LAL) assay (Chromogenix AB, Mölndal, Sweden). The estimated levels of endotoxin were as follows: M-blocks: 0.24 ng/mg; poly M: 0.25 ng/mg; G-blocks: 12.4 ng/mg; C60XY: 1.12 ng/mg.

Lipopolysaccharide and detoxified LPS (D-LPS) from smooth *Salmonella minnesota* were purchased from Sigma. D-LPS had been prepared by alkaline deacylation of LPS through the removal of the ester linked fatty acids (Ding et al, *J. Med. Microbiol.* 1990, 31:95).

The characteristics of the polysaccharides are summarized in Table 1 below.

The characteristics of the polysaccharides are summarized in Table 1 below.

TABLE 1

Characteristics of the polyuronic acids used in this study

| Polysaccharide | Source | Molecular weight | Monomer Composition |
|---|---|---|---|
| poly M | *P. a.** | 350,000 | 92% D-ManA, 8% L-GulA |
| M-blocks | *P. a.** | <5,500 | 94% D-ManA, 6% L-GulA |
| G-blocks | *A. v.*** | 5,500 | 94% L-GulA, 6% D-ManA |
| C60XY | Cellulose | 30,000 | 88% D-GlcA, 12% D-Glc |

*) *P. a.* = *Pseudomona aeruginosa*
**) *A. v.* = *Actobacter vinelandii*

Covalent coupling of uronic acids and D-LPS to particles

Magnetic monodisperse polystyrene (PS) particles with epoxy groups (Ugelstad et al, *Progress in Polymer Science,* 1992, 17:87) were aminated as described by Hermanson et al (Immunobilized Affinity Ligand Techniques, Academic Press 1992). In some experiments hydrophilic bovine serum albumin (BSA, Sigma) particles were prepared according to the method described by Longo et al (*J. Pharm. Sci.* 1992, 71:1323). Uronic acids and D-LPS were coupled to magnetic monodisperse- or BSA particles through formation of amide bonds between the carboxylic groups on the uronic acids and primary amine groups on the particles. The coupling was carried out in 0.1M phosphate buffer, pH 7.3, by adding carbodiimide EDC (1-ethyl-3-(3-dimethlaminpropyl)carbodiimide) and sulfo-NHS (N-hydroxysulfosuccinimide) as described by Staros et al (*Anal. Biochem.* 1986, 156:200). After linking the polysaccharide to the particles, they were extensively washed in 0.1M phosphate buffer, pH 10 in order to remove noncovalently bound polysaccharide. For some experiments particles made of crosslinked bovine serum albmin were made. The amounts of M- and G-blocks covalently linked to the particles were estimated by measuring the radioactivity in a β-counter (Packard). The characteristics of the particles used and the amount of M-blocks and G-blocks coupled to them are given in Table 2 below.

TABLE 2

Characteristics of the beads used in this study and the amount of covalently linked M-blocks and G-blocks

| Particle type | φ [μm] | Surface [μm$^2$] | Primary aminogroups on the surface [mmol/g] | Amount of M-blocks [ng/10$^6$ beads] | Amount of G-blocks [ng/10$^6$ beads] |
|---|---|---|---|---|---|
| PS 1 | 4.5 | N.D. | 0.65 | 33 | N.D. |
| PS 2 | 4.2 | 2.3 | 0.11 | 12 | 17 |
| PS 3 | 4.5 | 3.8 | 0.50 | 50 | 47 |
| PS 4 | 4.5 | 3.8 | 0.36 | 43 | 54 |
| BSA | 5–10 | N.D. | N.D. | 117 | N.D. |

ND = not determined

Monocyote cultivation

Monocytes were isolated from A+blood buffycoat (The Blood Bank, University Hospital, Trondheim, Norway) as described by Bøyum (*Scand. J. Immunol.* 1976, 5:9). Monolayers of monocytes in 24-well culture plates (Costar, Cambridge, Mass.) were cultured in AIM serum-free medium (Gibco) with 1% glutamine and 40 µm/ml Garamycin. Different concentrations of particles and polysaccharides in solution were added to monocytes, and supernatants were harvested 8 hours later and assayed from TNF activity in the WHI clone 13 bioassay (Espevik et al, *J. Immunol. Methods*, 1986, 95:99).

SW480/β-gal cultivation

Human colon adenocarcinoma cells, SW480/β-gal (donated by Dr. Gerald Ranges, Miles Inc., West Haven, Conn., USA), contain a beta galactosidase (β-gal) gene under control of the cytomegalovirus (CMV) immediate early promoter/enhancer region (Galloway et al, *Eur. J. Immunol* 1992, 22:305). SW480/β-gal were grown in RPMI 1640 (Gibco Laboratories, Paisley, Scotland), supplemented with 2 mM L-glutamine, 10% heat-inactivated FCS (HyClone, Logan, Utah, USA) and 40 µg/ml Garamycin (FCS medium). Stimulation with particulate and soluble forms of M-blocks and different forms of LPS was carried out in RPMI 1640 medium supplemented with glutamine, 20% human A+serum (The Blood Bank, University Hospital of Trondheim, Trondheim, Norway) and Garamycin (A+medium). The β-galactosidase assay was performed essentially as described previously (Løegreid et al *J. Biol. Chem.* 1995. 270:25418). Substrate conversion was measured as optical density (OD) at 570 nm.

TNF assay

TNF activity was determined by measuring its cytotoxic effect on the fibrosarcoma cell line WEHI 164 clone 13 as described by Espevik et al (*J. Immunol. Methods* 1986, 95:99). Dilutions of recombinant human TNF (donated by Dr. Refaat Shalaby, Genentech, South San Francisco, Calif.) were included as a standard. The TNF specificity of the assay was verified by use of a neutralizing Mab against recombinant human TNF (Liabakk et al, *J. Immunol Methods*, 1990, 134:253). The results are presented as pg/ml ±SD for triplicate determinations.

EXAMPLE 1

The purpose of this experiment was to test whether the TNF-inducing potency of poly M was affected by its form.

Radiolabelled poly M with MW of 350,000 was degraded by acid hydrolysis by the process described above to obtain polysaccharide fragments (M-blocks) with an MW of 5.5 kD. The resultant M-blocks were covalently linked by the procedure described above, to the two types of polystyrene particles, namely PS 2 and PS 3 (see Table 2 above).

The TNF-inducing potency of the two particle- bound M-blocks was then determined by the TNF assay described above, and compared to that of unlinked M-blocks, and also to unhydrolysed poly M in phosphate- buffered saline solution. The results are shown in FIG. 1A.

As can be seen from FIG. 1A, reduction of the polymer size to 5.5 kD reduced the TNF inducing potency by a factor of 10–100. However, covalently linking the 5.5 kD M-blocks to PS 2 or PS 3 particles resulted in a 2500 and 60,000 times increase, respectively, in the TNF inducing potency compared to soluble M-blocks. Linking M-blocks to particles also potentiated the TNF response compared to poly M in solution.

The experiment was repeated, but with the amino groups on the particles substituted with carboxyl groups. It was found that this substitution did not change the TNF release from monocytes. This therefore indicates that the stimulatory effect of M-blocks linked to particles is not caused by a net negative charge on the particles or a non-specific reaction due to the coupling procedure.

COMPARATIVE EXAMPLE 1

Example 1 was repeated but with 5.5 D G-blocks prepared as described above. The results are shown in FIG. 1B.

It is seen by FIG. 1B that G-blocks in solution or linked to PS 2 particles did not induce the monocytes to produce TNF.

This experiment demonstrates that binding to a substrate a polysaccharide which inherently does not exhibit a capability of stimulating an immune response has no effect on this characteristic of the substance.

EXAMPLE 2

The TNF assay was repeated on LPS and detoxified LPS (both obtained from Sigma). The reagents were added as solutions. As in Example 1, M-blocks were used as a control.

Figure 2A:
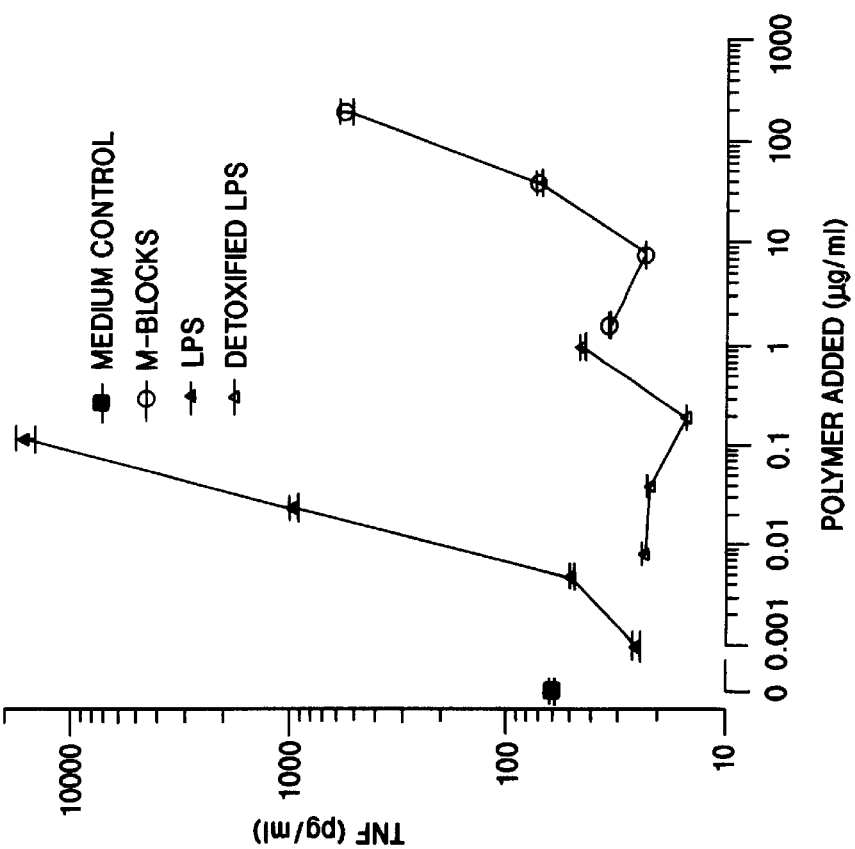

As shown in FIG. 2A, when tested on monocytes in solution under serum free condition it was found that the detoxified LPS (D-LPS) up to 1 µg/ml did not induce monocytes to produce TNF, whereas the untreated LPS gave a strong TNF response.

However, when in accordance with the present invention the D-LPS was linked covalently to PS 1 particles (see Table 2 above) and the TNF assay was repeated it was found that there was a high production of TNF, comparable with the M-block particles of Example 1 (FIG. 2B).

Since the molecular weights of M-blocks and D-LPS are comparable, and since D-LPS also was linked to the particles by amine bonds implicate that the amount of D-LPS bound is equal or less than the amount of M-blocks bound to the particles. The data thus shows that lower MW fragments from polysaccharides are very potent TNF inducers when presented for monocytes on the surface of particles.

COMPARATIVE EXAMPLE 2

Figures 3A, 3B:
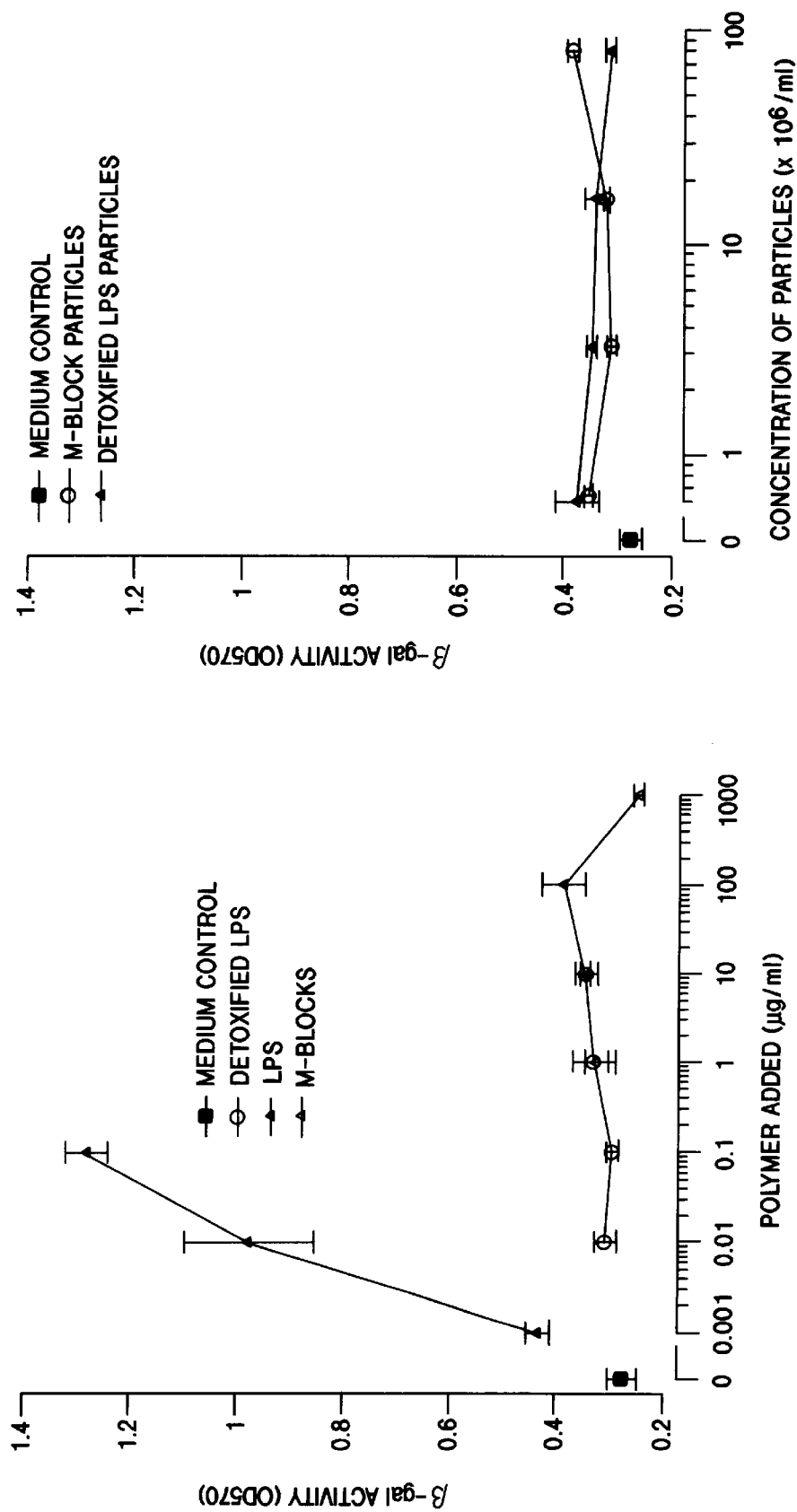
FIGS. 3A and 3B show activation of human CMV promoter by products in Comparative Example 2.

The SW480-βgal cells do not express functional membrane CD14, but respond to LPS in the presence of serum. It was therefore of interest to study if D-LPS or M-blocks, either in solution or linked to particles according to the present invention, were able to activate these cells. As can be seen from FIG. 3A, the complete LPS gave a strong and dose related activation of the human CMV promoter in the SW480-βgal cells, whereas D-LPS or M-blocks in solution had no stimulatory effect. In addition, M-block and D-LPS bound to PS .1 polystyrene particles had no stimulatory effect on this cell type (FIG. 3B). This data indicate that M-block and D-LPS particles have a preference in stimulating membrane CD14 positive monocytes and no LPS responsive cells which lack membrane CD14.

EXAMPLE 3

The TNF assay was repeated with another member of the uronic acid family, D-glucuronic acid (D-GlcA) polymer. Such polymers are known to stimulate monocytes to produce TNF in a CD14-dependent manner, although with less potency as compared to poly M.

A polymer consisting of 88% D-GlcA and 12% D-Glc, and with an MW of 30,000, was prepared by oxidizing cellulose by the method described above.

The TNF assay was conducted both on the D-GlcA polymer in phosphate buffered saline solution (1–2 ml/mg) and also on the polymer covalently bound to PS 2 particles in accordance with the present invention. The results are shown graphically in FIG. 4.

It will be noted that the D-GlcA polymer in solution resulted in a low production of TNF. However, the D-GlcA bound to the PS 2 polystyrene particles showed a marked increase in TNF production.

Figure 4:
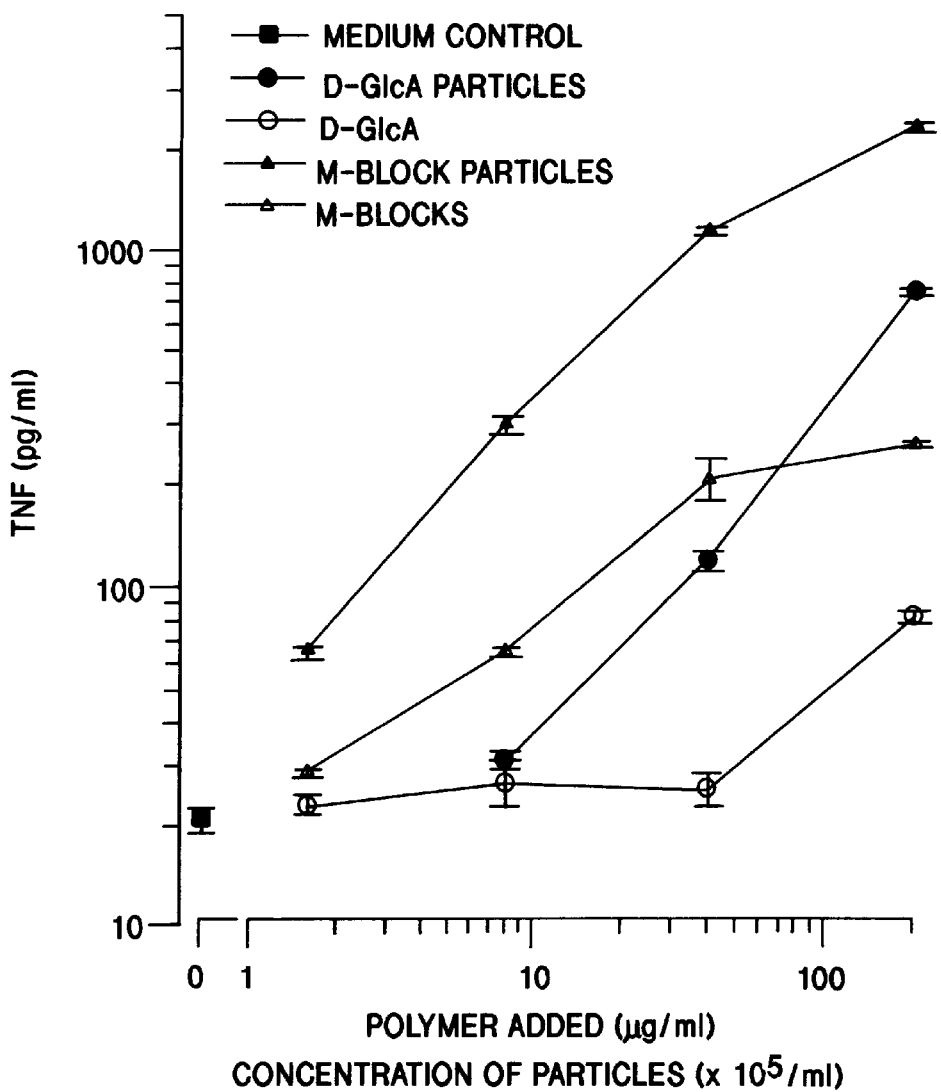
FIGS. 4 and 5 show results for TNS assays on products in Examples 3 and 4, respectively.

In FIG. 4, the results for the M-blocks are shown for comparison purposes.

EXAMPLE 4

The purpose of this experiment was to test whether TNF-stimulating activity would be exhibited by mannuronan fragments of very low molecular weight if they were covalently bound to bioabsorbable particles in accordance with this invention.

The TNF assay was therefore repeated on M-blocks with an MW of around 3,000, prepared as described hereinabove. The resulting low molecular weight oligomer was covalently bound to BSA particles (see Table 2 above) by the method described above. The results of the TNF assay on the particle-bound oligomer are shown in FIG. 5.

Figure 5:
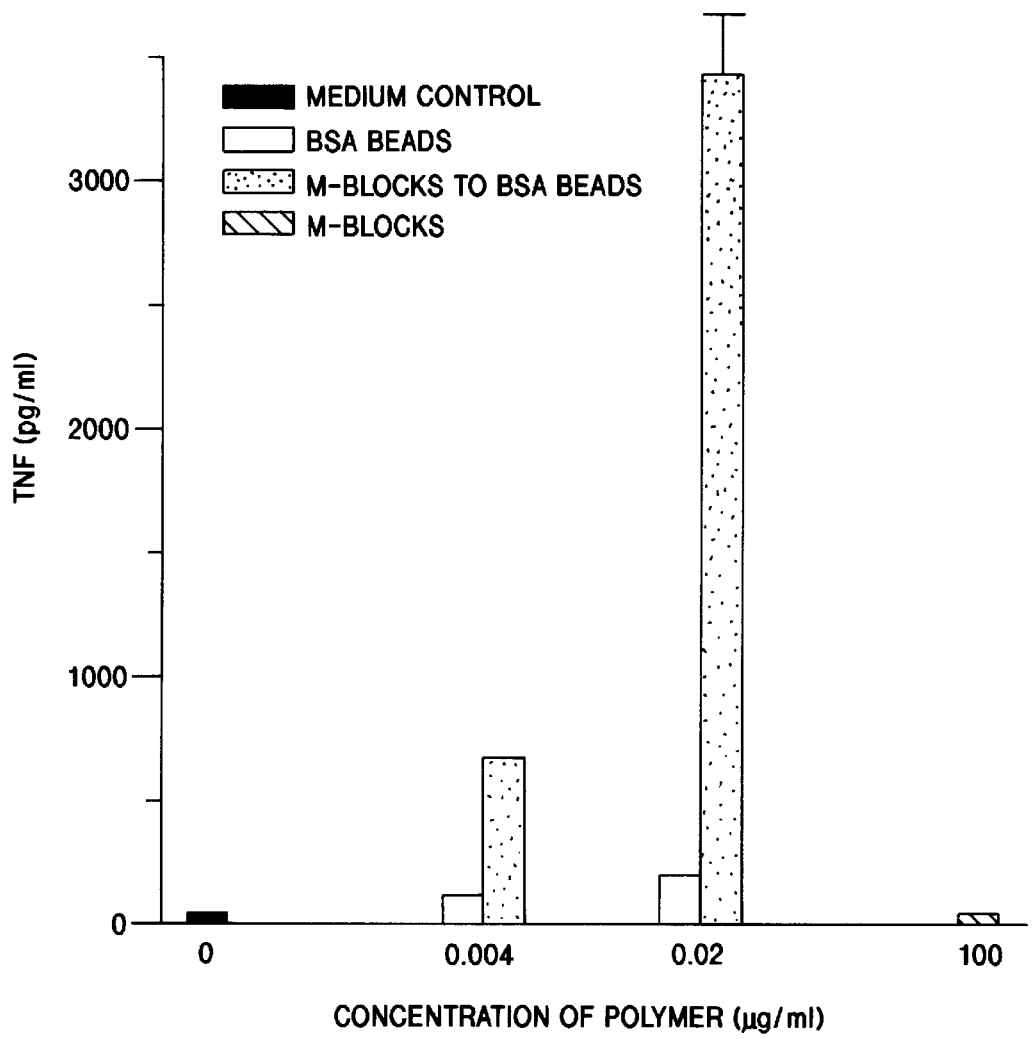

It will be seen from FIG. 5 that adding soluble M-blocks to monocytes did not result in production of TNF even at a concentration of 100 μg/ml. However, adding M-block-BSA particles in accordance with this invention resulted in more than 1 ng/ml of TNF at a polymer concentration equivalent to 0.02 μg/ml. Even at a polymer concentration equivalent to 0.004 μg/ml there was significant production of TNF.

What is claimed is:

1. A pharmaceutically acceptable substrate material to a surface of which is chemically bound a cytokine-stimulating bioactive substance selected from the group consisting of fragments of polysaccharides, other than β-1,3-D glucan, and fragments of bacterial nucleic acids.

2. A substrate material according to claim 1, wherein said bioactive substance is a polysaccharide fragment containing from 2–100 sugar units.

3. A substrate material according to claim 2, wherein said polysaccharide fragment contains from 10–30 sugar units.

4. A substrate material according to one of claims 1–3, wherein said bioactive substance is a 1–4 linked uronic acid polymer.

5. A substrate material according to claim 4, wherein said bioactive substance contains more than 80 % mannuronic acid residues.

6. A substrate material according to claim 4, wherein said bioactive substance is detoxified lipopolysaccharide.

7. A substrate material according to any one of claims 1–3, wherein said substrate is in the form of particles.

8. A substrate material according to claim 7, wherein said particles have a size up to 50 μm.

9. A substrate material according to claim 8, wherein said particles have a size up to 5 μm.

10. A substrate material according to any claim 7, wherein said particles are surface-modified polystyrene particles or albumin particles.

11. A substrate material according to any one of claims 1–3, wherein said bioactive substance is covalently coupled to said substrate surface.

12. A pharmaceutical composition suitable for injection, comprising a substrate material according to any one of claim 7 and a pharmaceutically acceptable injectable carrier therefor.

13. A method for potentiating the cytokine-stimulating effect of an immune-stimulating bioactive substance selected from the group consisting of fragments of polysaccharides, other than β-1,3-D glucan, and fragments of bacterial nucleic acids, wherein said bioactive substance is contacted with a pharmaceutically acceptable substrate so as to become chemically bound to a surface thereof.

14. A method according to claim 13, wherein said bioactive substance is a polysaccharide fragment containing from 2–100 sugar units or a 1–4 linked uronic acid polymer.

15. A method according to claim 13, wherein said substrate is in the form of particles.

16. A method according to claims 13 or 14, wherein said bioactive substance is covalently linked to said substrate surface.

17. A substrate material according to claim 4, wherein said substrate is in the form of particles.

18. A substrate material according to claim 5, wherein said substrate is in the form of particles.

19. A substrate material according to claim 6, wherein said substrate is in the form of particles.

20. A substrate material according to claim 8, wherein said particles are surface-modified polystyrene particles or albumin particles.

21. A substrate material according to claim 9, wherein said particles are surface-modified polystyrene particles or albumin particles.

22. A substrate material according to claim 4, wherein said bioactive substance is covalently coupled to said substrate surface.

23. A substrate material according to claim 5, wherein said bioactive substance is covalently coupled to said substrate surface.

24. A substrate material according to claim 6, wherein said bioactive substance is covalently coupled to said substrate surface.

25. A substrate material according to claim 7, wherein said bioactive substance is covalently coupled to said substrate surface.

26. A substrate material according to claim 8, wherein said bioactive substance is covalently coupled to said substrate surface.

27. A substrate material according to claim 9, wherein said bioactive substance is covalently coupled to said substrate surface.

28. A substrate material according to claim 10, wherein said bioactive substance is covalently coupled to said substrate surface.

29. A pharmaceutical composition suitable for injection, comprising a substrate material according to claim 8 and a pharmaceutically acceptable injectable carrier therefor.

30. A pharmaceutical composition suitable for injection, comprising a substrate material according to claim 9 and a pharmaceutically acceptable injectable carrier therefor.

31. A pharmaceutical composition suitable for injection, comprising a substrate material according to claim 10 and a pharmaceutically acceptable injectable carrier therefor.

32. A method according to claim 13 or 14, wherein said particles have a size up to 50 μm.

33. A method according to claim 13 or 14, wherein said particles have a size up to 5 μm.

34. A method according to claim 13 or 14, wherein said particles are surface-modified polystyrene particles or albumin particles.

35. A method according to claim 15, wherein said bioactive substance is covalently linked to said substrate surface.

36. A substrate material according to claim 1, wherein the fragment is detoxified LDS.

37. A substrate material according to claim 1, wherein the fragment is a fragment of mannuronan.

38. A method according to claim 13, wherein the fragment is detoxified LDS.

39. A method according to claim 13, wherein the fragment is a fragment of mannuronan.

* * * * *